US011752615B2

(12) United States Patent
Mann et al.

(10) Patent No.: US 11,752,615 B2
(45) Date of Patent: Sep. 12, 2023

(54) COUPLER FOR BLADES AND HANDLES

(71) Applicant: Creative Edge Medical, LLC, Homer Glen, IL (US)

(72) Inventors: Rachel Mann, Atlanta, GA (US); Sydney Platt, Brookhaven, GA (US); Bailey Klee, Denver, CO (US); Nicholas Quoc Quan, Richmond Hill, GA (US)

(73) Assignee: Creative Edge Medical, LLC, Homer Glen, IL (US)

( * ) Notice: Subject to any disclaimer, the term of this patent is extended or adjusted under 35 U.S.C. 154(b) by 1197 days.

(21) Appl. No.: 16/295,508

(22) Filed: Mar. 7, 2019

(65) Prior Publication Data

US 2019/0275660 A1    Sep. 12, 2019

Related U.S. Application Data

(60) Provisional application No. 62/639,820, filed on Mar. 7, 2018.

(51) Int. Cl.
*A61B 17/3213* (2006.01)
*B25G 3/18* (2006.01)
(Continued)

(52) U.S. Cl.
CPC ............ *B25G 3/18* (2013.01); *A61B 17/3213* (2013.01); *A61B 17/3215* (2013.01);
(Continued)

(58) Field of Classification Search
CPC ............ A61B 17/3213; A61B 17/3217; A61B 17/3215; A61B 17/00473; A61B 2090/0801; B26B 5/00
(Continued)

(56) References Cited

U.S. PATENT DOCUMENTS 4,180,162 A    12/1979    Magney
4,746,016 A    5/1988    Pollak et al.
(Continued)

FOREIGN PATENT DOCUMENTS

DE    102009007292 A1 *    7/2010    ......... A61B 17/3213
DE    102009007292 A1    7/2010
(Continued)

OTHER PUBLICATIONS

International Search Report and Written Opinion for International Application No. PCT/US20190/021104 dated May 22, 2019 (13 pages).
(Continued)

*Primary Examiner* — Nhat Chieu Q Do
(74) *Attorney, Agent, or Firm* — Eversheds Sutherland (US) LLP

(57) ABSTRACT

A device is provided for coupling and decoupling a blade and a handle, wherein the device includes a housing that defines an interior chamber and an exterior slot adjacent the interior chamber. The exterior slot is dimensioned to pass the blade and is configured to receive a portion of the handle. The housing defines a groove in the interior chamber configured to retain the blade in a ready configuration for coupling the blade to the handle. The device includes a pivot member secured within the interior chamber of the housing. The pivot member is pivotable between an unlocked configuration and a locked configuration. The unlocked configuration of the pivot member is configured to allow the blade in the ready configuration to be coupled to the handle. The locked configuration of the pivot member is configured to lock the blade within the interior chamber.

22 Claims, 7 Drawing Sheets

(51) Int. Cl.
*B26B 5/00* (2006.01)
*A61B 17/3215* (2006.01)
*A61B 17/3217* (2006.01)
*A61B 90/00* (2016.01)
*A61B 17/00* (2006.01)

(52) U.S. Cl.
CPC ............ *A61B 17/3217* (2013.01); *B26B 5/00* (2013.01); *A61B 2017/00473* (2013.01); *A61B 2090/0801* (2016.02)

(58) Field of Classification Search
USPC .......................................................... 206/355
See application file for complete search history.

(56) References Cited

U.S. PATENT DOCUMENTS

| | | | |
|---|---|---|---|
| 4,903,390 A | 2/1990 | Vidal et al. | |
| 5,363,958 A | 11/1994 | Horan | |
| 5,699,908 A | 12/1997 | Frye et al. | |
| 5,938,027 A * | 8/1999 | Soroff | A61B 17/3215 206/370 |
| 6,216,868 B1 * | 4/2001 | Rastegar | A61B 17/3217 206/370 |
| 6,605,100 B1 | 8/2003 | Shan et al. | |
| 7,155,795 B2 | 1/2007 | Abidin et al. | |
| 2006/0168819 A1 * | 8/2006 | Perreault | B26B 1/046 30/161 |
| 2013/0079804 A1 | 3/2013 | Milton et al. | |
| 2017/0027602 A1 | 2/2017 | Austria | |
| 2017/0100151 A1 | 4/2017 | Severns et al. | |
| 2017/0360523 A1 | 12/2017 | Khajavi et al. | |
| 2019/0069919 A1 * | 3/2019 | Swoish | A61B 17/3213 |

FOREIGN PATENT DOCUMENTS

| | | | |
|---|---|---|---|
| WO | 96/07363 A1 | 3/1996 | |
| WO | 2013/142897 A1 | 10/2013 | |
| WO | WO-2018148793 A1 * | 8/2018 | ......... A61B 17/3213 |

OTHER PUBLICATIONS

"Health Care Logistics 9830 Surgical Blade Remover, Non-Sterile—100 Per Pack," Web page <https://Hand Tools, Web page <http://www.devinemedical.com/9830-Surgical-Blade-Remover-Non-Sterile-p/hcl-9830.htm>, 1 page, retrieved from the internet on Aug. 21, 2020.

"Swann Morton No. 10 Scalpel Blades 100-count Box, No. 3 Handle, Blade Remover Box & Resusable Safety Cap: Industrial ...," Web page <https://us.amazon.com/Swann-Morton-Scalpel-100-count-Reusable/dp/B00DNW2E10.htm>, 7 pages, retrieved from the internet on Aug. 21, 2020.

"Qlicksmart BladeFLASK—Single-Handed Scalpel Blade Remover," Web page <https://www.qlicksmart.com/product/bladeflask-scalpel-blade-remover/>, 4 pages, retrieved from the internet on Aug. 25, 2020.

"(1) Scalpel Blade Remover, Standard—Nifty Medical Supplies Inc.," Web page <https://www.niftymedical.ca/products/scalpel-blade-remover-standard>, 2 pages, retrieved from the internet on Aug. 25, 2020.

"Swann-Morton Surgical Blade Remover," Web page <https://www.swann-morton.com/product/116.php>, 3 pages, retrieved from the internet on Aug. 25, 2020.

"Pivit Palm-Sized Disposable Blade Remover | Large Capacity Holds 150 to 300 Blades," Web page <https://www.amazon.com/Palm-Sized-Disposable-Capacity-Protection-Infection/dp/B07CSBXBY5, 6 pages, retrieved from the internet on Aug. 25, 2020.

* cited by examiner

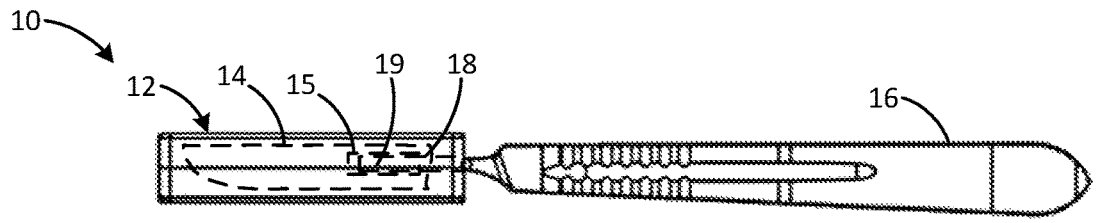
FIG. 1A
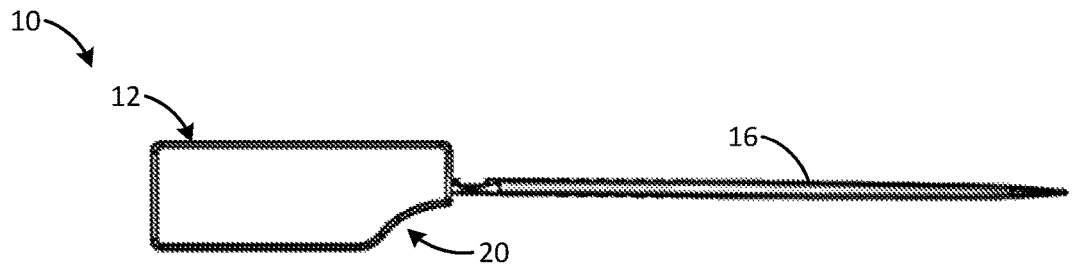
FIG. 1B
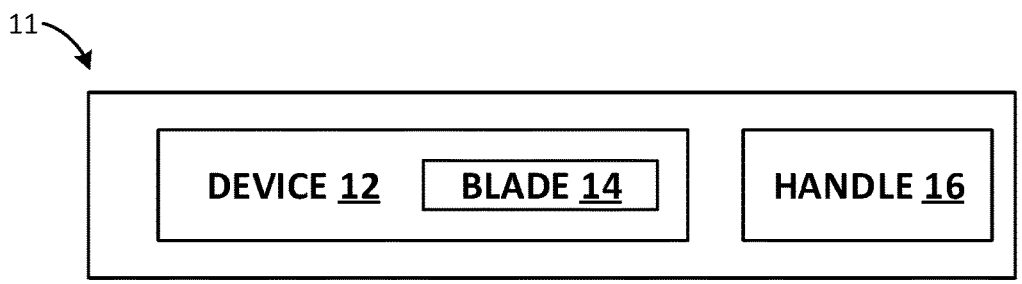
FIG. 1C
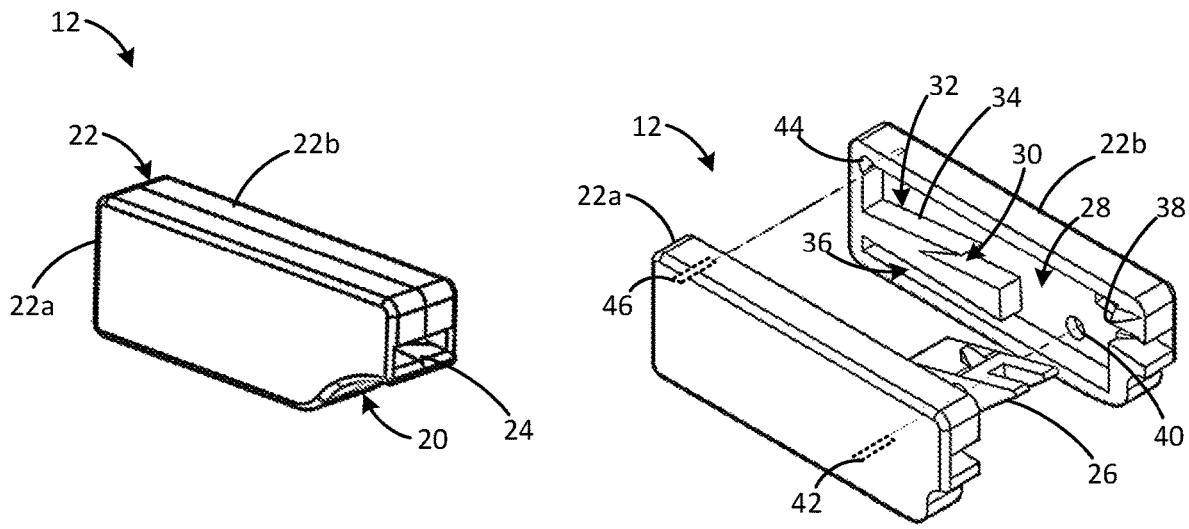
FIG. 1D  FIG. 1E

COUPLER FOR BLADES AND HANDLES

This application claims the benefit of U.S. Provisional Application No. 62/639,820 filed on Mar. 7, 2018, which is incorporated herein by reference.

BACKGROUND

1. Technical Field

The disclosure relates generally to blades, and in particular, devices for coupling and decoupling blades and handles, such as those of surgical scalpels.

2. Description of the Related Art

Surgical scalpels are routinely used to introduce tissue incisions and openings. The scalpels include a reusable handle on which replaceable blades are armed prior to use. Blades are removed and discarded after every use to maintain hygiene and sterility. Surgical blades and other types of blades can cause injury during scalpel preparation, blade attachment, use, handoff, blade removal, or disposal, or any time when the blade is exposed.

A need remains for improved methods, devices, and systems for handling blade attachment and removal, for scalpel preparation and handoff, for disposal of used blades, and for storage, management, and inventory control of blades within surgical suites, hospitals, or other environments.

SUMMARY

The disclosure describes devices, assemblies, and kits for coupling and decoupling a blade and a handle.

In embodiments, a device for coupling and decoupling a blade and a handle includes a housing. The housing defines an interior chamber, a groove in the interior chamber, and an exterior slot adjacent the interior chamber. The exterior slot is dimensioned to pass the blade through the exterior slot. The exterior slot is configured to receive a portion of the handle from an exterior of the housing into the interior chamber. The groove is configured to retain the blade in a ready configuration for coupling the blade to the handle. The device further includes a pivot member secured within the interior chamber of the housing. The pivot member is pivotable between an unlocked configuration and a locked configuration. The unlocked configuration of the pivot member is configured to allow the blade in the ready configuration to be coupled to the handle. The locked configuration of the pivot member is configured to lock the blade within the interior chamber.

A user (for example, a clinician, an assistant, a medical service provider, an industrial or commercial operator, or a hobbyist) may operate the device to one or more of 1) arm the handle with the blade, 2) handoff the armed blade to another user, 3) disarm the blade from the handle, and 4) house the used disarmed blade. The device may allow coupling, handoff, and decoupling of the blade and the handle while reducing or avoiding direct handling or contact with the blade.

BRIEF DESCRIPTION OF THE DRAWINGS

FIG. 1A is a conceptual top view of an assembly including a device for coupling and decoupling a blade and a handle.

FIG. 1B is a conceptual side view of the assembly of FIG. 1A.

FIG. 1C is a conceptual block diagram showing a kit including the device and handle of FIG. 1A.

FIG. 1D is a conceptual plan view of the device of FIG. 1A, showing a housing of the device defining an exterior slot.

FIG. 1E is a conceptual exploded view of the device of FIG. 1A, showing a pivot member secured between housing members of a housing of the device.

Figure 2A:
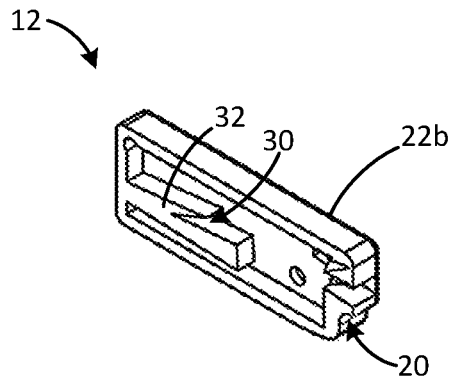
FIG. 2A is a conceptual partial view of the housing of the device of FIG. 1A, with the pivot member removed.

It is to be understood that the invention is not limited in its application to the details of construction and the arrangement of components illustrated in the drawings or set forth in the following description.

DETAILED DESCRIPTION

A device for coupling and decoupling a blade and a handle includes a housing. The housing defines an interior chamber, a groove in the interior chamber, and an exterior slot adjacent the interior chamber. The exterior slot is dimensioned to pass the blade through the exterior slot. The exterior slot is configured to receive a portion of the handle from an exterior of the housing into the interior chamber. The groove is configured to retain the blade in a ready configuration for coupling the blade to the handle. The device further includes a pivot member secured within the interior chamber of the housing. The pivot member is pivotable between an unlocked configuration and a locked configuration. The unlocked configuration of the pivot member is configured to allow the blade in the ready configuration to be coupled to the handle. The locked configuration of the pivot member is configured to lock the blade within the interior chamber. In embodiments, the pivot member may itself lock the blade, or co-operate with another component of the device to lock the blade, or may otherwise facilitate locking of the blade in the device. In embodiments, the transition from the unlocked configuration to the locked configuration of the pivot member is configured to disarm the blade from the handle. In embodiments, the pivot member may not lock the blade, and a different component or portion of the device may lock the blade after or upon disarming.

A user may arm the blade on the handle by inserting a portion of the handle, for example, a distal end of the handle, into the device. For example, the user may insert the handle until the blade clicks onto the handle, or until the handle cannot be further inserted. Subsequently, the user may withdraw an assembly including the handle armed with the blade and proceed to use the assembly. Alternatively, the user may handoff the armed blade to another user. In embodiments, the user may reinsert the armed blade into the device, flipped over to another side, to shield the armed blade within the device during handoff. After handoff or use, a user may insert the used blade into the device, until the blade clicks off the device, resulting in disarming or decoupling of the blade from the handle. The used blade is retained within the device, and the user may discard the used blade and device.

In embodiments, the device is configured to transition between an unlocked configuration and a locked configuration. The unlocked configuration allows the blade in the ready configuration to be coupled to the handle. The locked configuration locks the blade within the interior chamber.

In embodiments, the device is configured to secure the blade in a first position and a second position different from the first position. The blade in the first position is in the groove, allowing the blade to be coupled to the handle. The blade is received from the handle in the second position and cannot be rearmed to the handle in the second position.

In embodiments, a sterile package may include one or both of the device or the handle, to maintain the device or the handle in a sterile environment before use. In embodiments, a kit may include the device and the handle. Thus, for example, a clinician may use the kit in an operating theater, surgical room, or another clinical environment to access the device and the handle.

Thus, devices, assemblies, and kits according to the disclosure may allow coupling, handoff, and decoupling of the blade and the handle while reducing or avoiding direct handling or contact with the blade. For example, a single device may be used for one or more of both arming and disarming of scalpels, or for protecting users during use or handoff, or for disposal after bade use. Devices, assemblies, and kits according to the disclosure may reduce time and complexity of use, by providing a relatively simpler and efficient process for arming, handoff, or disarming. For example, a user may operate the device in a "single-click" operation for arming, handoff, or disarming. Devices, assemblies, and kits according to the disclosure may facilitate avoiding reuse of used blades. For example, a used blade disarmed from a handle and stored in a device cannot be re-armed onto the handle. A used blade may be stored in a different configuration, for example, at a different angle or spatial configuration, compared to a fresh blade ready for arming, and the different configuration of the used blade may prevent re-arming of the used blade onto the handle.

While devices, assemblies, and kits according to the disclosure may be used in clinical environments, they may also be used in veterinary environments, morgues, forensics, medical schools, dental applications, craft, construction, industrial applications, or any other suitable applications.

FIG. 1A is a conceptual top view of an assembly 10 including a device 12 for coupling and decoupling a blade 14 and a handle 16. FIG. 1B is a conceptual side view of assembly 10 of FIG. 1A. Blade 14 may include any type of blade configured to be mounted to handle 16, for example, a surgical blade, a cosmetic blade, a shaving blade, a hobby blade, a craft blade, a utility blade, or the like. Blade 14 may be substantially rigid, and define a sharp edge. Blade 14 may define one or more of a slot, groove, opening, protrusion, boss, or pedestal, or the like for engaging with or disengaging from a portion of handle 16 to couple or decouple blade 14 from handle 16. For example, handle 16 may define a distal end 18 configured to receive or engage with and hold blade 14. Distal end 18 of handle 16 may define a one or more of a slot, groove, opening, protrusion, boss, or pedestal, or the like configured to securely engage with blade 14 to cause blade 14 to be retained on handle 16. In embodiments, blade 14 defines a blade slot 15, and a portion of handle 16 defines a raised boss 19 configured to be received by blade slot 15. Exterior slot 24 of housing 22 is configured to receive raised boss 19 of the portion of handle 16.

Handle 16 may be elongated, and be substantially cylindrical, flat, ridged, or otherwise define ergonomic textures, contours, or surfaces. One or both of blade 14 or handle 16 may include one or more of metal, alloy, glass, ceramic, polymer, composites, or any combinations thereof. The metal or alloy may include hardened and tempered steel, stainless steel, high carbon steel, or titanium. In some examples, handle 16 includes stainless steel. One or both of blade 14 or handle 16 may include one or more coatings.

In some examples, blade 14 includes a surgical scalpel, and handle 16 includes a scalpel handle. For example, blade 14 may include a standard surgical blade such as nos. 6, 9, 10, 10a, 11, 11P, E11, 12, 12D, 13, 14, 15, 15A, 15C, 15T, D/15, 16, 17, 18, 19, 20, 21, 22, 22A, 23, 24, 25, 25A, 26, 27, 34, 36, 40, PM 40, PM40B, 60, PM60, or PM60B. Handle 16 may include a standard surgical handle compatible with blade 14, for example, a "Bard-Parker" handle such as nos. 2, 3, B3, 3 graduated, 3 long, 4, 4 graduated, 4 long, 5, 6, 7, 9, or PM8.

Device 12 may house blade 14 in an unused, fresh, sterile, or ready configuration, as shown in FIG. 1A. A user may insert a portion of blade 16, for example, distal end 18, into device 12 to engage blade 14 with handle 16, or arm handle 16 with blade 14. The user may withdraw handle 16 armed with blade 14 from device 12. As described elsewhere in the disclosure, after use, the user may deposit used blade 14 into device 12 by inserting armed blade 14 and handle 16 into device 12 to cause disarming of blade 14 from handle 16.

Device 12 may include one or more features to facilitate holding or gripping during use. For example, device 12 may define an ergonomic grip 20. Ergonomic grip 20 may include one or more curved or contoured surfaces depressed into or raised from an adjacent surface of device 12, and dimensioned to accommodate a finger or portion of a user's hand or a portion of a holding implement. In embodiments, ergonomic grip 20 may include one or more of a smooth region, a textured region, a ridged region, a stippled region, a coated region, a rubberized region, or the like.

FIG. 1C is a conceptual block diagram showing a kit 11 including device 12 and handle 16 of FIG. 1A. Device 12 may be pre-loaded with blade 14. Kit 11 may include a flexible, semi-rigid, or rigid container or packaging for holding device 12 and handle 16. For example, the container may include one or more of metal, alloy, polymer, glass, ceramic, woven fabric, or nonwoven fabric.

In embodiments, kit 11 includes a sterile package including device 12 including blade 14, and handle 16. The sterile package may include any suitable medical packaging maintaining device 12, blade 14, and handle 16 in a sterile environment before use. In other embodiments, kit 11 or device 12 itself may act as a package, and no additional packaging may be required. In embodiments, device 12 or kit 11 may be shrink-wrapped with a polymeric material.

In some embodiments, kit 11 or device 12 may not be pre-sterilized. In some such embodiments, blade 14 and handle 16 may be sterilized after arming handle 16 with blade 14, and prior to use.

FIG. 1D is a conceptual plan view of device 12 of FIG. 1A, showing a housing 22 of device 12 defining an exterior slot 24. Exterior slot 24 is dimensioned to receive and pass one or both of blade 14 or a portion of handle 16 into or from housing 22 of device 12. For example, exterior slot 24 is dimensioned to pass blade 14 through exterior slot 24 and to receive a portion (for example, distal end 18) of handle 16 from an exterior of housing 22 into interior chamber 26. Exterior slot 24 may define any suitable linear, curved, or complex perimeter, surface, or contour configured to accommodate blade 14 or the portion of handle 16.

Housing 22 may include one or more of a flexible, semi-rigid, or rigid material. In some embodiments, all components of device 12, including housing 22 and other components within housing 12, are rigid. The material may include at least one of a metal, an alloy, a glass, a polymer, a ceramic, or a composite. In embodiments, the alloy includes a steel or a titanium alloy. Housing 22 may include a molded, additively manufactured, stamped, embossed, or machined material. In some embodiments, housing 22 includes an injection molded polymeric material. In some examples, the polymer includes one or more of polycarbonate, ABS (acrylonitrile butadiene styrene), a thermoplastic elastomer, a silicone, PMMA (polymethylmethacrylate), a nylon, a fluoropolymer, a polyester, a polyalkylene, a polypropylene, a polyurethane, or any other suitable polymer, copolymer, or polymer blend. In some embodiments, housing 22 may be opaque, translucent, or transparent, or include one or more opaque, translucent, or transparent regions. For example, housing 22 may be substantially opaque and include a translucent or transparent window or windows. In embodiments, housing 22 includes a transparent or translucent wall configured to permit visual determination whether blade 14 is in the ready configuration.

Housing 22 may provide a puncture-proof barrier to house blade 14 during arming, handoff, disarming, and disposal of blade 14. For example, all sharp sides of blade 14 may be encapsulated or shielded by housing 22, and the only part of blade 14 accessible to the user is a dull portion or end of blade 14 to be mated with or coupled with handle 16.

In some embodiments, housing 22 includes a unitary structure. In some embodiments, housing 22 includes at least two members. For example, housing 12 may include two housing members 22a and 22b, which are secured together. In some embodiments, housing members 22a and 22b are removably secured together, such that housing members 22a and 22b are separable without destroying or damaging device 12. In some such embodiments, housing members 22a and 22b may be reassembled after separation. In other embodiments, housing members 22a and 22b are permanently secured together, for example, by a permanent adhesive, weld, or clip, such that housing members 22a and 22b cannot be separated without damaging or destroying device 12, or otherwise without affecting the integrity of device 12. In some such examples, housing members 22a and 22b cannot be reassembled after separation.

Figure 2B:
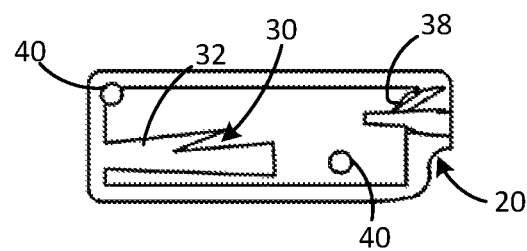
FIG. 2B is a conceptual partial side view of the housing of FIG. 2A.
Figure 3A:
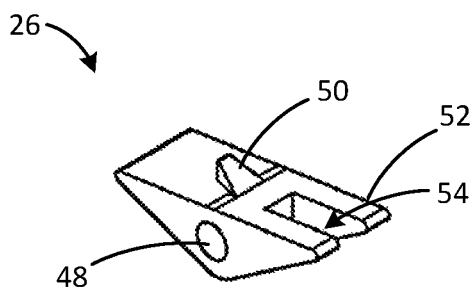
FIG. 3A is a conceptual plan view of an example pivot member.
Figure 3B:
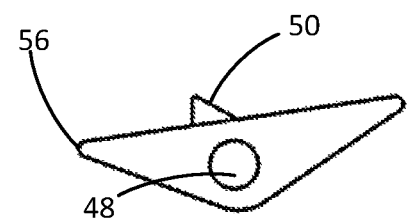
FIG. 3B is a conceptual side view of the pivot member of FIG. 3A.
Figure 4A:
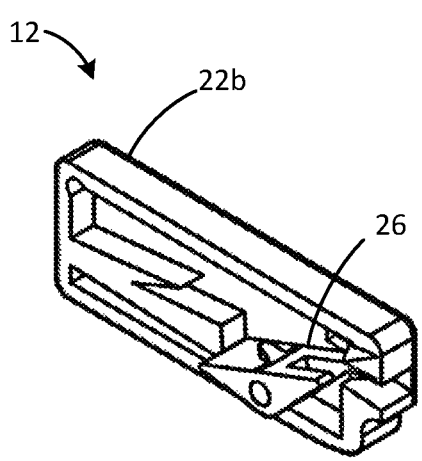
FIG. 4A is a conceptual partial view of the device of FIG. 1A, with the pivot member retained in the housing.
Figure 4B:
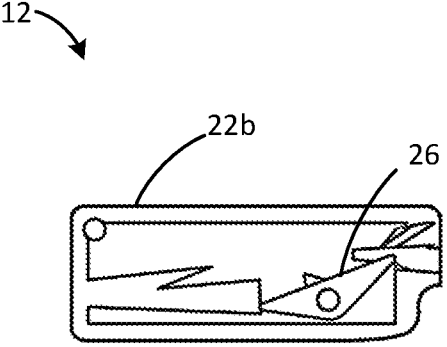
FIG. 4B is a conceptual side view of the device of FIG. 4A.

FIG. 1E is a conceptual exploded view of device 12 of FIG. 1A, showing a pivot member 26 secured between housing members 22a and 22b of housing 22 of device 12. FIGS. 2A to 3B further illustrate housing 22 and pivot member 26. FIG. 2A is a conceptual partial view of housing 22 of device 12 of FIG. 1A, with pivot member 26 removed. FIG. 2B is a conceptual partial side view of housing 22 of FIG. 2A. FIG. 3A is a conceptual plan view of pivot member 26. FIG. 3B is a conceptual side view of pivot member 26 of FIG. 3A. FIG. 4A is a conceptual partial view of device 12 of FIG. 1A, with pivot member 26 retained in housing 22. FIG. 4B is a conceptual side view of device 12 of FIG. 4A. Components of device 12 are described with reference to the various views shown in FIGS. 1A to 4B.

Pivot member 26 may include any material described with reference to housing 22. Housing 22 and pivot member 26 may include the same or different selection of the materials described with reference to housing 22. Pivot member 26 is pivotable between an unlocked configuration and a locked configuration, as described elsewhere in the disclosure. The unlocked configuration of pivot member 26 is configured to allow blade 14 in a ready configuration to be coupled to handle 16. The locked configuration of pivot member 26 is configured to lock blade 14 within an interior chamber 28 defined by housing 22. In embodiments, housing 22 defines interior chamber 28 between interior facing surfaces of housing members 22a and 22b. Interior chamber 28 is fluidically coupled to exterior slot 24. Interior chamber 28 is dimensioned to hold blade 14 in a ready configuration for arming onto handle 16, and to receive and hold used blade 14 from handle 16 upon disarming.

Housing 22 defines a groove 30 in interior chamber 28. Groove 30 is configured to retain blade 14 in a ready configuration for coupling blade 14 to handle 16. In embodiments, blade 14 retained on groove 30 is sterile. Groove 30 may include one continuous and smooth surface or contour, or may include multiple angled surfaces or contours. In some embodiments, groove 30 includes two flat surfaces that meet at a predetermined angle. In some such embodiments, groove 30 may maintain blade 14 in a ready configuration for arming between the two flat surfaces. For example, a sharp end of blade 14 may rest between the flat surfaces and may contact a vertex between the flat surfaces of groove 30. Thus, groove 30 is configured to retain blade 14, for example, a sterile or fresh blade, in a ready configuration for coupling blade 14 to handle 16. In embodiments, groove 30 is oriented relative to exterior slot 24 to cause raised boss 19 of the portion of handle 16 to engage with blade slot 15 in response to receiving the portion of handle 16 through exterior slot 24. For example, groove 30 may be angled relative to exterior slot 24 so that raised boss 19 extends through blade slot 15 at an angle when distal end 18 of handle 16 is introduced and advanced through exterior slot 24. Device 12 may thus be configured to, in response to receiving the portion of handle 16 through exterior slot 24 into interior chamber 28 of housing 22, couple blade 14 in the ready configuration from 30 groove to handle 16.

In some embodiments, groove 30 may be defined by a unitary portion of housing 22, such a rest 32 defined by housing 22. For example, rest 32 may extend from an interior surface of housing 22 within interior chamber 28. In some embodiments, rest 32 extends less than halfway into interior chamber 28. In other embodiments, rest 32 extends about halfway, or more than halfway, into interior chamber 28. In some embodiments, rest 32 may not be continuous or unitary with housing 22, and may include a portion that is adhered, attached, welded, or secured to housing 22. For example, housing 22 may include a first unitary portion, while rest 32 may include a second unitary portion distinct from the first unitary portion.

In some embodiments, rest 32 defines at least one free surface within interior chamber 14. For example, groove 30 may include the at least one free surface of rest 32.

Rest 32 may also define a shelf 34, for example, adjacent groove 30. In some embodiments, groove 30 is dimensioned to hold blade 14 in a ready configuration for arming, while shelf 34 is dimensioned to hold blade 14 in a used configuration after disarming. In some embodiments, a lower surface of rest 32 may be spaced from opposing shelf 34 such that groove 30 is between the lower surface and shelf 34. For example, a gap 36 may space rest 32 from an adjacent surface of interior chamber 28. In other embodiments, gap 36 may not exist, and rest 32 may be continuous with an adjacent portion of housing 22.

Exterior slot 24 is dimensioned to pass blade 14 through exterior slot 24, for example, into interior chamber 28. In some embodiments, exterior slot 24 is configured to receive a portion of handle 16, for example, distal end 18 of handle 16, from an exterior of housing 22 into interior chamber 28. Device 12 may include a lip 38 that extends or protrudes inwards into interior chamber 28 adjacent exterior slot 24. Lip 38 may promote or assist in disarming, locking, biasing, or retaining blade 14 within interior chamber 28. In embodiments, housing 22 (for example, one or both of housing member 22a and housing member 22b) define lip 38.

Housing 22 may define openings or recesses and complementary pins or protrusions for securing two or more members of housing 22 or components in interior chamber 28 to housing 28. For example, housing 22 may include opening 40 and pin 42 for securing pivot member 26. Housing 22 may include one or multiple pairs of opening 44 and pin 46 for securing housing member 22a to housing member 22b. Such openings and pins may be disposed along a perimeter of housing 22, or at any other suitable portion of housing 22. Housing 22 may thus permit pivot member 26 to pivot during arming or disarming.

Pivot member 26 includes a pivot slot 48 between a first end 52 and a second end 56 of pivot 26. Pin 42 may extend through pivot slot 48 and through opening 40 of housing 22 to pivotably secure pivot member 26 in housing 22. For example, pivot member 26 may pivot about pin 42 passing through pivot slot 48. Pivot member 26 may define protrusion 50 for guiding or aligning one or both of blade 14 or handle 16, for example, distal end 18 of handle 16. Protrusion 50 may be dimensioned to pass through blade opening 15 of blade 14. First end 52 of pivot member 26 facing exterior slot 24 may define a cutout 54. Cutout 54 may be a channel that aligns handle 16 with blade opening 15 of blade 14 during arming or disarming. For example, while pivot member 26 pivots about pin 42, distal end 18 of handle 16 may be aligned through cutout 54. In embodiments, prongs defined by cutout 54 adjacent cutout 54 may contact and lift off blade 14 from handle 16 during disarming. Second end 56 may be adjacent to an end 58 of rest 32 during arming and disarming, and may contact or move relative to end 58 as pivot member 26 pivots about pin 42.

The configuration and operation of device 12 including arming and disarming of blade 14 and handle 16 are further described with reference to FIGS. 5A to 7D. For example, FIGS. 5A to 6B illustrate stages of arming of blade 14 onto handle 16, while FIGS. 7A to 7D illustrate stages of disarming of blade 14 from handle 16.

Figure 5A:
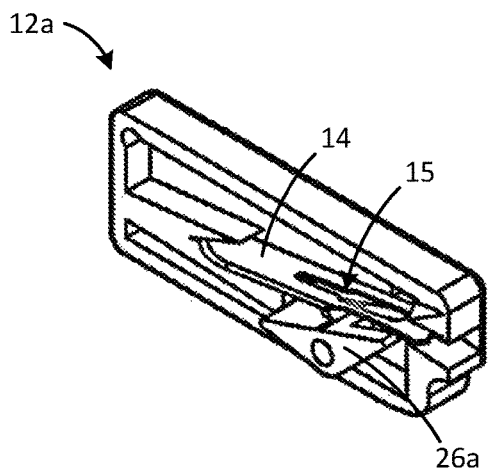
FIG. 5A is a conceptual partial plan view of the device of FIG. 1A in a ready configuration.
Figure 5B:
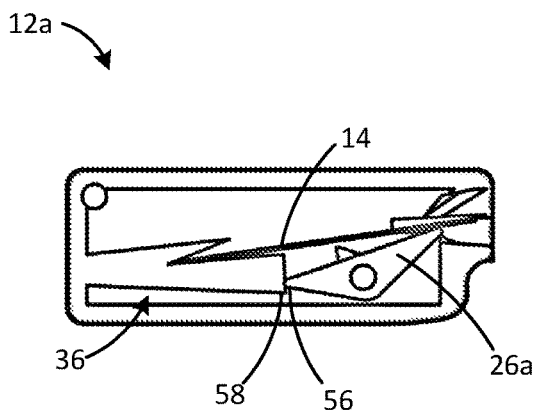
FIG. 5B is a conceptual side view of the device of FIG. 5A in the ready configuration.

FIG. 5A is a conceptual partial plan view of device 12 of FIG. 1A in a ready configuration 12a. FIG. 5B is a conceptual side view of device 12 of FIG. 5A in ready configuration 12a. In ready configuration 12a, blade 14 is retained along groove 30. A distal tip of blade 14 may be securely held or placed at or adjacent to an end or vertex of groove 30. Groove 30 is angled relative to external slot 24 to maintain blade 14 in a predetermined angle and orientation relative to external slot 24. For example, groove 30 may be angled toward external slot 24 by more than about 5° relative to a horizontal axis along device 12. In some embodiments, groove 30 is angled at about 7°, for example, at 7.63°. In ready configuration 12a, an upper surface of pivot member 26, for example, the major surface extending between first end 52 and second end 56, may incline at substantially the same angle as groove 30. For example, both groove 30 and the major surface of pivot member 26 may be inclined at 7.63° in ready configuration 12a. In other embodiments, the major surface of pivot member 26 may incline at a different angle relative to groove 30.

Figure 6A:
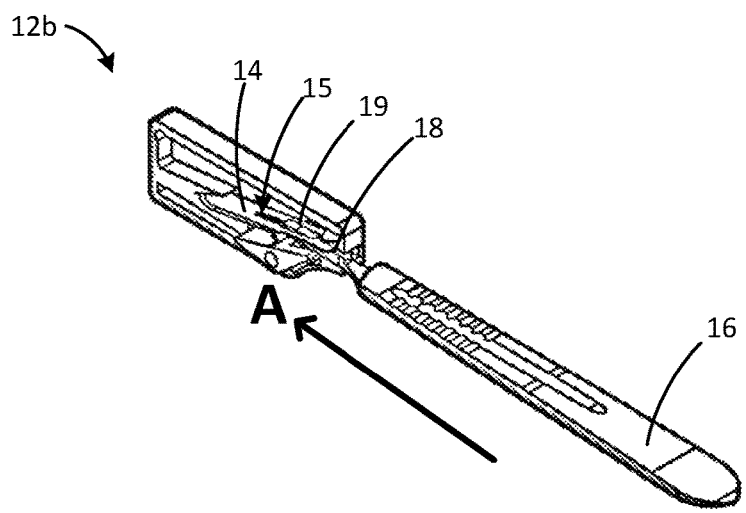
FIG. 6A is a conceptual partial plan view of an assembly including a handle inserted into the device of FIG. 1A in an arming configuration for arming a blade onto the handle.
Figure 6B:
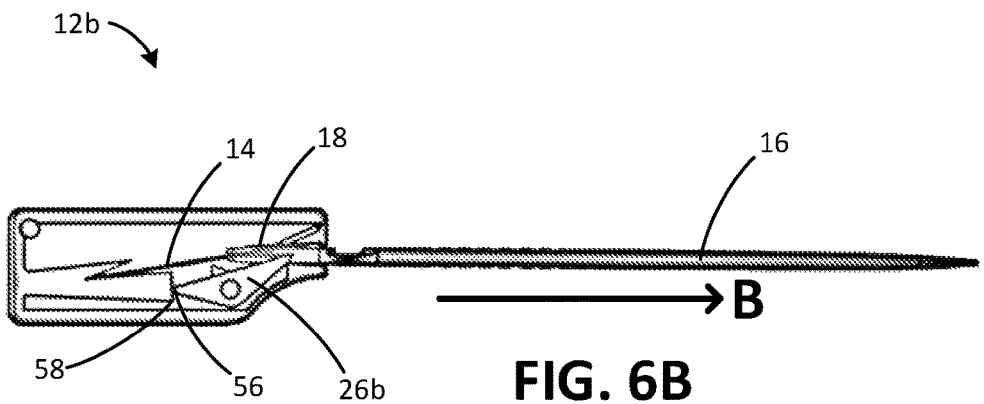
FIG. 6B is a conceptual side view of the assembly of FIG. 6A in the arming configuration.

FIG. 6A is a conceptual partial plan view of an assembly including handle 16 inserted into device 12 of FIG. 1A in arming configuration 12b. FIG. 6B is a conceptual side view of the assembly of FIG. 6A in arming configuration 12b. During arming, a user may insert distal end 18 of handle 16 through exterior slot 24 into interior chamber 28 of housing 22 in a single linear motion, as indicated by arrow A in FIG. 6A. During arming, distal end 18 passes through cutout 54 of pivot member 26 and through blade opening 15 of blade 14. Cutout 54 aligns distal end 18 so that blade 14 securely contacts handle 16. A raised feature, for example, a boss, at distal end 18, may engage in blade opening 15. The user may perceive a click or another tactile or audible signal in response to arming of blade 14 on handle 16. Handle 16 may be withdrawn in a single linear motion, as indicated by arrow B in FIG. 6B, to cause blade 14 armed on handle 16 to be withdrawn with handle 16. At end of the arming, second end 56 of pivot member 26 is retained above end 58 of rest 32, as shown in FIG. 6B.

Armed blade 14 and handle 16 are ready for use after arming. If armed blade 14 is to be handed off or held prior to use, blade 14 and handle 16 may be reinserted into exterior slot for handoff, flipped over to the opposite side. Thus, after withdrawing armed blade 14, the user may turn or flip blade 14 and handle 16, and reinsert blade 14 into exterior slot 24 to shield sharp edges or portions of blade 14. The shielded blade 14 and handle 16 may be handed off to another user or held in a tool, prior to use, without exposing armed blade 14.

After arming or handoff, used blade 14 may be decoupled from handle 16 by reinserting blade 14 in the same orientation as during arming into exterior slot 24 of device 12.

Figure 7A:
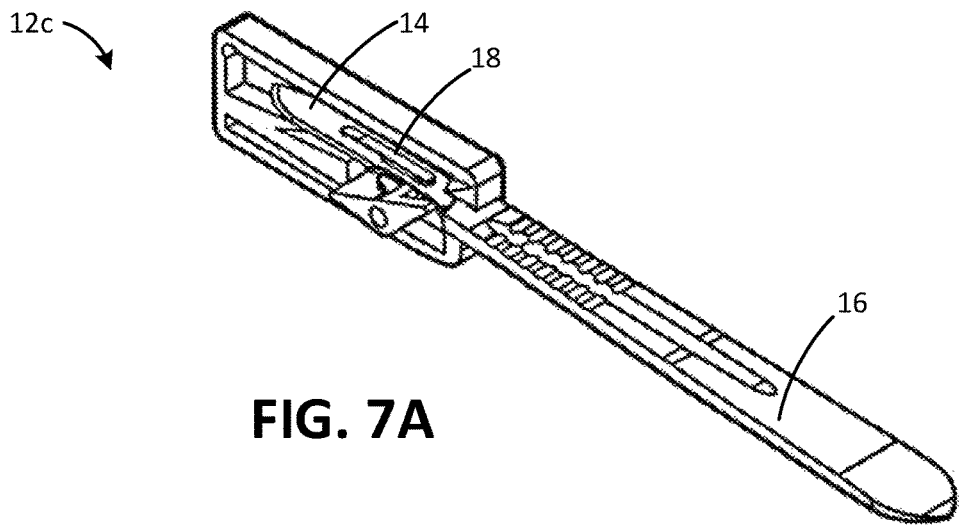
FIG. 7A is a conceptual partial plan view of an assembly including a handle inserted into the device of FIG. 1A in a preliminary disarming configuration for disarming a blade from the handle.
Figure 7B:
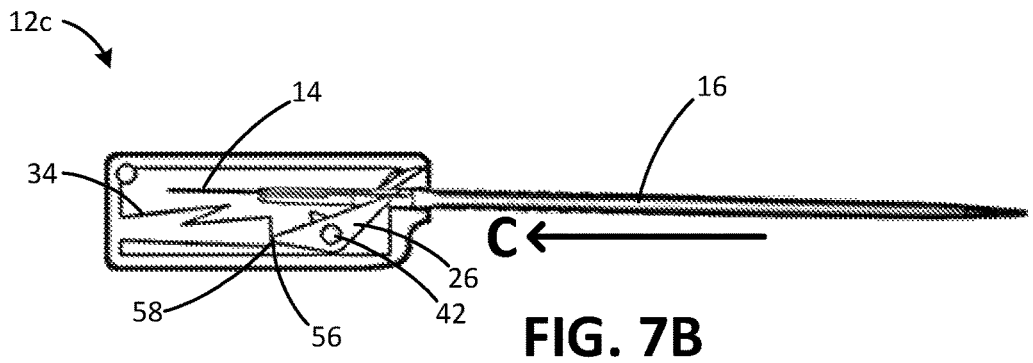
FIG. 7B is a conceptual side view of the assembly of FIG. 7A in the preliminary disarming configuration.

FIG. 7A is a conceptual partial plan view of an assembly including handle 16 inserted into device 12 of FIG. 1A in a preliminary disarming configuration 12c for disarming blade 14 from handle 16. FIG. 7B is a conceptual side view of the assembly of FIG. 7A in preliminary disarming configuration 12c. In preliminary disarming configuration 12c, the user inserts blade 14 in a single linear motion as indicated by arrow C in FIGS. 7A and 7B. In preliminary disarming configuration 12c, second end 56 of pivot member 26 remains above end 58 of rest 32.

Figure 7C:
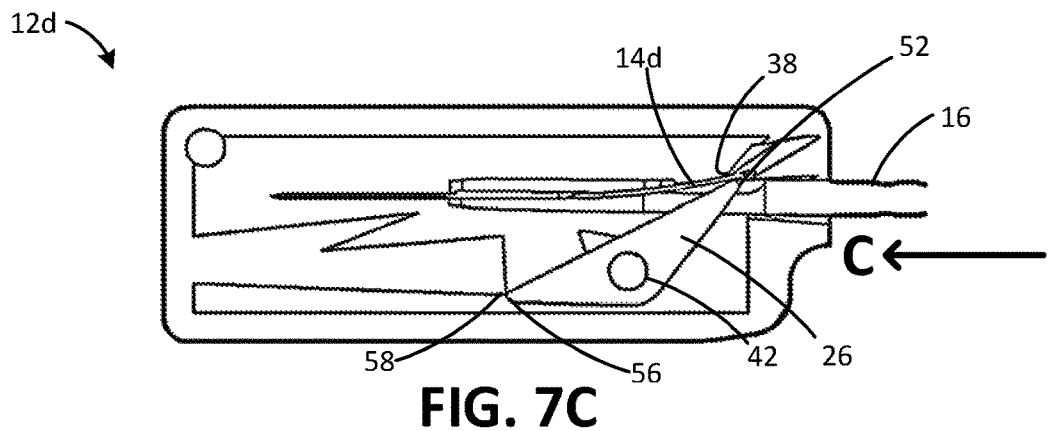
FIG. 7C is a conceptual side view of the assembly of FIG. 7A with a dull end of the blade deflected by the pivot member in an intermediate disarming configuration during disarming.

FIG. 7C is a conceptual side view of the assembly of FIG. 7A with a dull end of blade 14 deflected by pivot member 26 in an intermediate disarming configuration 12d during disarming. The single linear motion along arrow C continues in intermediate disarming configuration 12, and the continued motion causes pivot member 26 to pivot downward about pivot pin 42, and second end 56 of pivot member 26 to slide past end 58 of rest 32. The motion also causes first end 52 of pivot member 26 to catch blade 14 against lip 38, and lift blade 14 off handle 16.

Figure 7D:
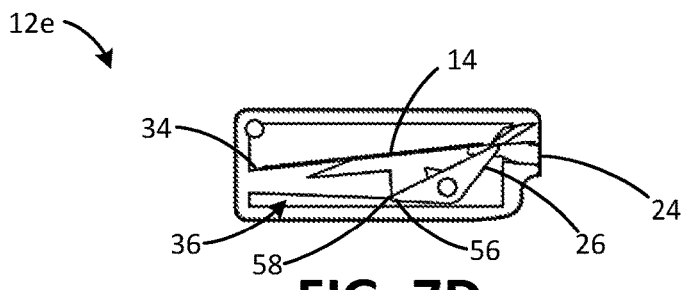
FIG. 7D is a conceptual side view of the device of FIG. 7A in a final disarmed configuration housing the disarmed blade.

FIG. 7D is a conceptual side view of device 12 of FIG. 7A in a final disarmed configuration 12e housing disarmed blade 14. In final disarmed configuration 12e, used blade 14 is retained on shelf 34 of rest 32. Pivot member 26 locks blade 14 in device 12, by blocking exterior slot 24. Pivot member 26 is maintained in the locked position by catching of second end 56 of pivot member 26 at gap 36, against end 58 of rest 32. Handle 16 is withdrawn from device 12. Device 12 including used blade 14 may be further processed or discarded.

In embodiments, pivot member 26 may itself lock blade 14, or co-operate with another component or portion of device 12 (for example, lip 38) to lock blade 14, or may otherwise facilitate locking of blade 14 in device 12. In embodiments, the transition from the unlocked configuration to the locked configuration of pivot member 26 is configured to disarm blade 14 from handle 16. For example, pivot member 26 may transition from the unlocked configuration to the locked configuration as device 12 transitions from ready configuration 12a to final disarmed configuration. In embodiments, pivot member 26 may not lock the blade, and a different component or portion of device 12 may lock blade 14 after or upon disarming.

One or more functions described with reference to pivot member 26 may be performed by other components or portions of device 12. In embodiments, device 12 may not include pivot member 26. In embodiments, device 12 may include a structure configured to move between an unlocked configuration and a locked configuration, or between an arming configuration and a disarming configuration. The unlocked configuration or arming configuration of the structure is configured to allow blade 14 in the ready configuration to be coupled to handle 16, and the disarming configuration or locked configuration of the structure is configured to disarm and/or lock blade 14 within interior chamber 28.

While pivot member 26 may pivot about its center, pivot member 26 may pivot about any portion of pivot member 26. Further, while pivot member 26 may pivot about pin 42, in other embodiments, device 12 may not include pivot pin 42, and instead, pivot member may pivot, flex, twist, shift, bend about a flexure point or region, or otherwise move, as described with reference to FIG. 8.

Figure 8:
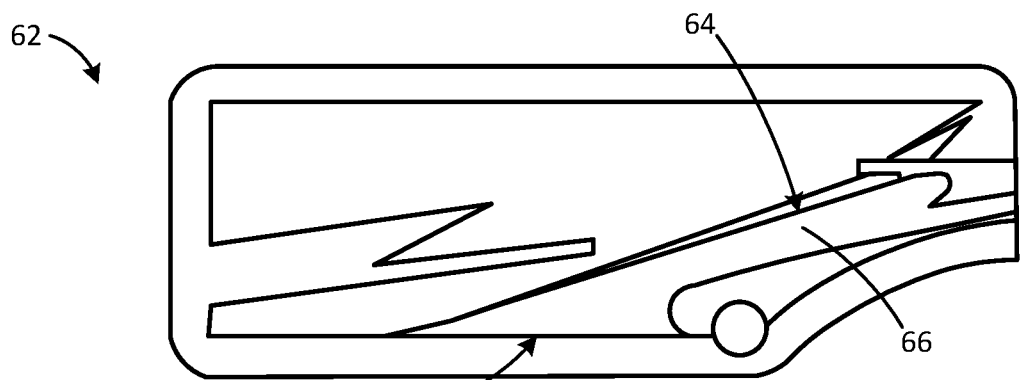
FIG. 8 is a conceptual partial side view of a device including a pivot member including a flexure.

FIG. 8 is a conceptual partial side view of a device 62 including a pivot member 64 including a flexure 66. Device 62 is similar to device 12 described with reference to FIGS. 1A to 7D in configuration and construction, with pivot member 64 differing from pivot member 26. In particular, pivot member 64 includes flexure 66, and does not include a pivot slot. Thus, pivot member 64 does not pivot about a pivot pin. Instead, flexure 66 of pivot member 64 pivots about a fixed end 68.

Optional variations in the configuration or structure of devices according to the disclosure are described with reference to FIGS. 9 to 13B. The devices, kits, or assemblies according to the disclosure may be modified to have any structure or component described with reference to FIGS. 9 to 13B.

Figure 9:
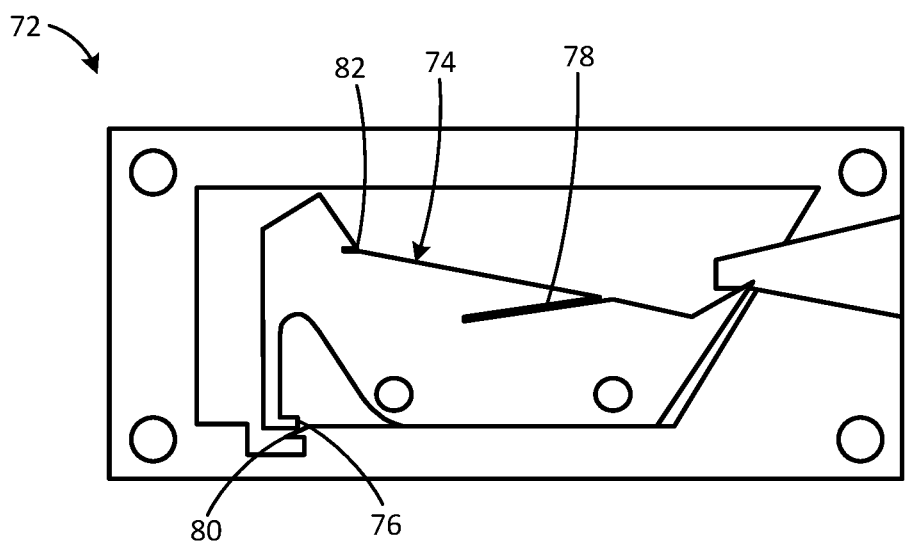
FIG. 9 is a conceptual partial side view of a device including a pivot member defining a notch or a slit.

FIG. 9 is a conceptual partial side view of a device 72 including a pivot member 74 defining a notch 76 or a slit 78. Upon rotation, notch 76 becomes latched in a groove 80 defined in a wall of device 72, therefore catching after pivoting of pivot member 74. Such catching prevents blade 14 from falling out of device 72 after blade removal.

Optional slit 78 is configured to house blade 14 in ready configuration 12a. In embodiments in which slit 78 is provided, groove 30 may be omitted. Slit 78 is inclined to retain blade 14 at an angle for engaging blade 14 with handle 16 for arming.

Pivot member 74 may include optional catch 82. During disarming, a distal tip of blade 14 may engage with catch 82 to cause pivot member to pivot and apply a vertical force to lift an end of blade 14 off handle 16 for disarming.

Figure 10:
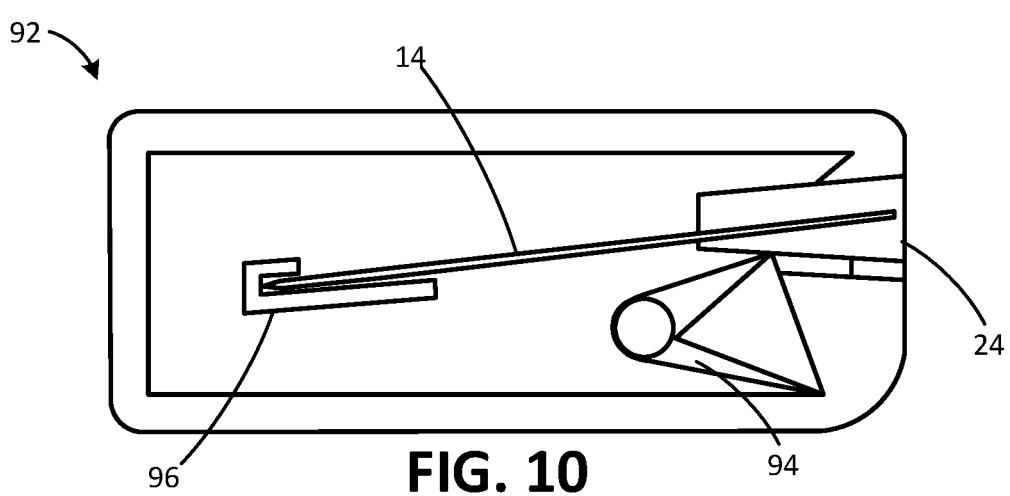
FIG. 10 is a conceptual partial side view of a device including a pivot member configured to lock against an exterior slot.

FIG. 10 is a conceptual partial side view of a device 92 including a pivot member 94 configured to lock against exterior slot 24. For example, upon disarming, pivot member 94 may pivot across exterior slot 24 so that blade 14 cannot be released through exterior slot 24. Pivot member 94 may be pronged.

Figure 11A:
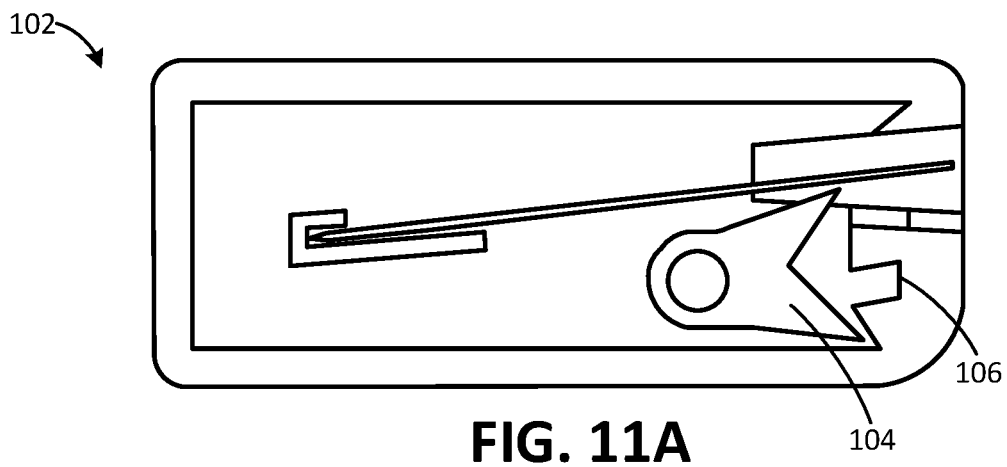
FIG. 11A is a conceptual partial side view of a device including a pivot member configured to engage with a locking notch defined by a housing of the device.

FIG. 11A is a conceptual partial side view of a device 102 including a pivot member 104 configured to engage with a locking notch 106 defined by a housing of device 102. Pivot member 104 is pronged, and a prong (for example, a bottom prong) engages with notch 106 upon pivoting of pivot member 104 to lock pivot member 104 upon disarming.

Figure 11B:
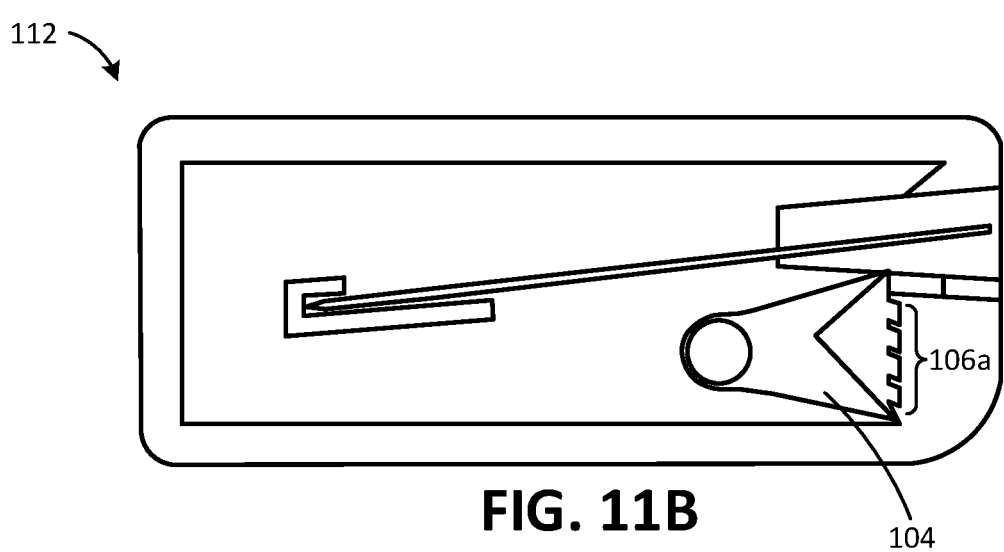
FIG. 11B is a conceptual partial side view of a device including a pivot member configured to engage with a plurality of locking notches defined by a housing of the device.

FIG. 11B is a conceptual partial side view of a device 112 including pivot member 102 configured to engage with a plurality of locking notches 106a defined by a housing of device 102. Device 112 operates similar to device 102 of FIG. 11A, but provides further tactile or audible feedback via plurality of notches 106a as a prong of pivot member 102 successively engages with notches 106a.

Figure 12:
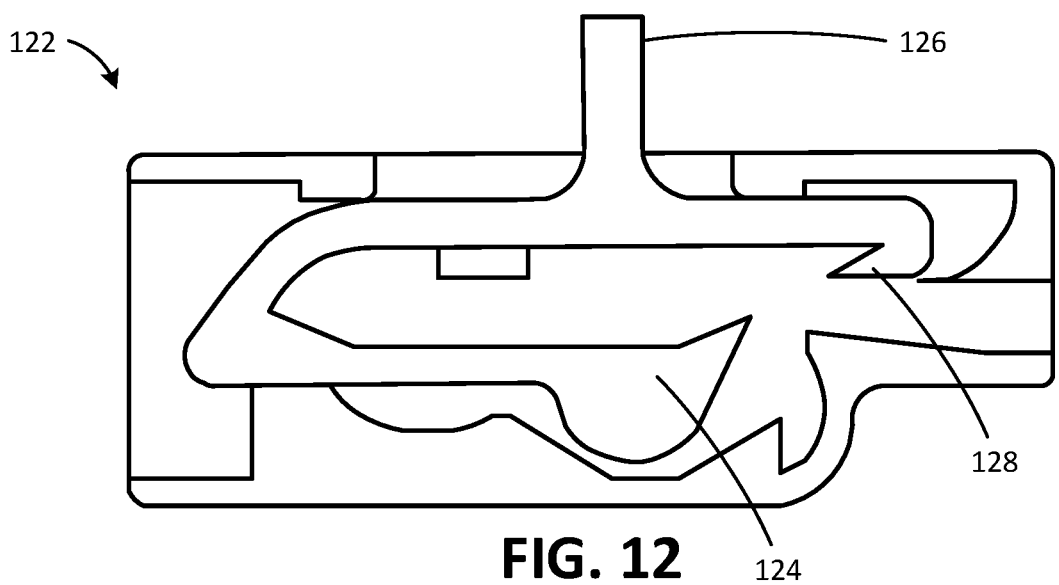
FIG. 12 is a conceptual partial side view of a device including a slidable pivot member.

FIG. 12 is a conceptual partial side view of a device 122 including a slidable pivot member 124. Slidable pivot member 124 defines a tab 126 that extends out through a window of device 122. The user can push or pull tab 126 by applying a horizontal force to cause pivot member 124 to be displaced along device 122. Pivot member 124 lifts off blade 14 off handle 16 as pivot member 124 is horizontally displaced.

Pivot member 124 may include optional catch 128 for catching blade 14 to facilitate disarming. For example, instead of lip 38, catch 128 may hold blade 14 against a different portion of pivot member 122 to facilitate removal of blade 14 from handle 16.

Figure 13A:
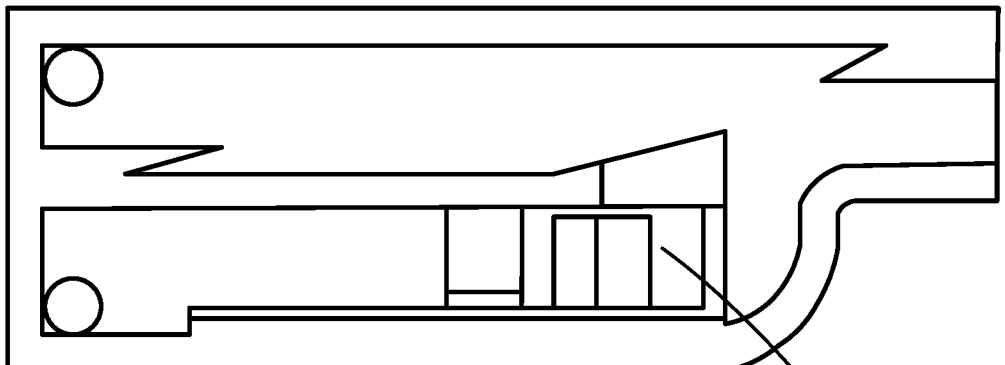
FIG. 13A is a conceptual partial side view of a device including a pinching member.
Figure 13B:
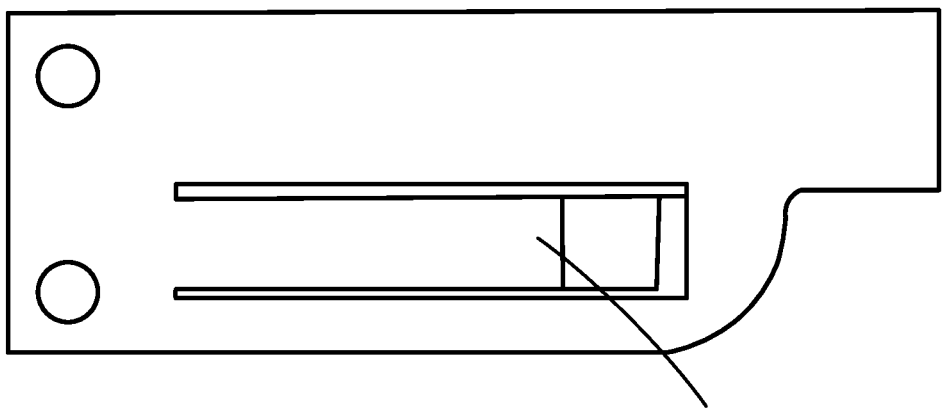
FIG. 13B is a conceptual external side view of the device of FIG. 13A.

FIG. 13A is a conceptual partial side view of a device 132 including a pinching member 134. FIG. 13B is a conceptual external side view of device 132 of FIG. 13A. The user can pinch pinching member 134 to cause blade 14 to lift off handle 16 for disarming.

Further optional variations or modifications to the devices, assemblies, and kits according to the disclosure are described. Rather than requiring the force of the user to cause rotation to lift the base of the blade for removal, a biasing element (for example, a spring) could be added to bias and lift blade off the handle for removal. Arming and disarming could occur in two different planes or even in two different regions or compartments within a device. A blade may be preloaded in a device in a slightly flexed or biased configuration so that upon insertion of the handle, the blade would unflex onto the handle to attach the blade to the handle. A blade may be preloaded in a slit in which the user has to determine the correct angle to insert the handle in order to attach the blade.

The following representative and non-limiting enumerated items describe embodiments according to the disclosure.

Item 1: A device for coupling and decoupling a blade and a handle, the device including:
a housing, where the housing defines:
an interior chamber, an exterior slot adjacent the interior chamber, where the exterior slot is dimensioned to pass the blade through the exterior slot, where the exterior slot is configured to receive a portion of the handle from an exterior of the housing into the interior chamber; a groove in the interior chamber, where the groove is configured to retain the blade in a ready configuration for coupling the blade to the handle; and a pivot member secured within the interior chamber of the housing, where the pivot member is pivotable between an unlocked configuration and a locked configuration, where the unlocked configuration of the pivot member is configured to allow the blade in the ready configuration to be coupled to the handle, and where the locked configuration of the pivot member is configured to lock the blade within the interior chamber.

Item 2: The device of item 1, where the blade defines a blade slot, where the portion of the handle defines a raised boss configured to be received by the blade slot, and where the exterior slot of the housing is configured to receive the raised boss of the portion of the handle.

Item 3: The device of item 2, where the groove is oriented relative to the exterior slot to cause the raised boss of the portion of the handle to engage with the blade slot in response to receiving the portion of the handle through the exterior slot.

Item 4: The device of any of items 1 to 3, where the portion of the handle includes a distal end of the handle.

Item 5: The device of any of items 1 to 4, where the device is configured to, in response to receiving the portion of the handle through the exterior slot into the interior chamber of the housing, couple the blade in the ready configuration from the groove to the handle.

Item 6: The device of any of items 1 to 5, where the device is configured to, in response to receiving the blade coupled to the handle through the exterior slot into the interior chamber of the housing, decouple the blade from the handle.

Item 7: The device of item 6, where the housing defines a shelf spaced from the groove, where the shelf is configured to receive the decoupled blade.

Item 8: The device of item 7, where the shelf defines a shelf axis, where the groove defines a groove axis, and where the shelf axis is inclined relative to the groove axis.

Item 9: The device of any of items 1 to 8, where the pivot member is configured to, in response to receiving the blade coupled to the handle through the exterior slot into the interior chamber of the housing, pivot to the locked configuration.

Item 10: The device of claim 1, where the pivot member includes a flexure configured to flex about a fixed end point.

Item 11: The device of any of items 1 to 10, where the device further includes a pivot pin in the interior chamber, and where the pivot member is configured to pivot about the pivot pin.

Item 12: The device of item 11, where the housing defines the pivot pin.

Item 13: The device of any of items 1 to 12, where the device further includes a lip adjacent the exterior slot, and where the lip is configured to co-operate with the pivot member in the locked configuration to lock the blade within the interior chamber.

Item 14: The device of item 13, where the housing defines the lip.

Item 15: The device of any of items 1 to 14, where at least one of the housing and the pivot member includes a rigid material.

Item 16: The device of item 15, where the rigid material includes at least one of a metal, an alloy, a glass, a polymer, a ceramic, or a composite.

Item 17: The device of any of items 1 to 16, where the housing includes a first housing member secured to a second housing member.

Item 18: The device of any of items 1 to 17, where the housing includes the blade retained in the groove in the interior chamber, and where the blade is sterile.

Item 19: The device of any of items 1 to 18, where the housing comprise a transparent or translucent wall configured to permit visual determination whether the blade is in the ready configuration.

Item 20: The device of any of items 1 to 19, further including the blade disposed in the interior chamber in the ready configuration.

Item 21: A sterile package including the device of any of items 1 to 20.

Item 22: A kit including the handle and the device of any of items 1 to 20.

Item 23: A device for coupling and decoupling a blade and a handle, the device including:
a housing, wherein the housing defines:
an interior chamber, an exterior slot adjacent the interior chamber, wherein the exterior slot is dimensioned to pass the blade through the exterior slot, wherein the exterior slot is configured to receive a portion of the handle from an exterior of the housing into the interior chamber, and a groove in the interior chamber, wherein the groove is configured to retain the blade in a ready configuration for coupling the blade to the handle; and a structure in the interior chamber configured to move between an unlocked configuration and a locked configuration, wherein the unlocked configuration of the structure is configured to allow the blade in the ready configuration to be coupled to the handle, and wherein the locked configuration of the structure is configured to lock the blade within the interior chamber.

Item 24: A device for coupling and decoupling a blade and a handle, the device including:
a housing, wherein the housing defines:
an interior chamber, an exterior slot adjacent the interior chamber, wherein the exterior slot is dimensioned to pass the blade through the exterior slot, wherein the exterior slot is configured to receive a portion of the handle from an exterior of the housing into the interior chamber, and a groove in the interior chamber, wherein the groove is configured to retain the blade in a ready configuration for coupling the blade to the handle;

wherein the device is configured to transition between an unlocked configuration and a locked configuration, wherein the unlocked configuration allows the blade in the ready configuration to be coupled to the handle, and wherein the locked configuration locks the blade within the interior chamber.

Item 25: A device for coupling and decoupling a blade and a handle, the device including:

a housing, wherein the housing defines:

an interior chamber, an exterior slot adjacent the interior chamber, wherein the exterior slot is dimensioned to pass the blade through the exterior slot, wherein the exterior slot is configured to receive a portion of the handle from an exterior of the housing into the interior chamber, and a groove in the interior chamber, wherein the groove is configured to retain the blade in a ready configuration for coupling the blade to the handle;

wherein the device is configured to secure the blade in a first position and a second position different from the first position, wherein the blade in the first position is in the ready configuration allowing the blade to be coupled to the handle, and wherein the blade is received from the handle in the second position and cannot be rearmed to the handle in the second position.

Item 26: A device for coupling and decoupling a blade and a handle, the device including:

a housing, wherein the housing defines:

an interior chamber, an exterior slot adjacent the interior chamber, wherein the exterior slot is dimensioned to pass the blade through the exterior slot, wherein the exterior slot is configured to receive a portion of the handle from an exterior of the housing into the interior chamber, and a groove in the interior chamber, wherein the groove is configured to retain the blade in a first position for coupling the blade to the handle;

wherein the device is configured to secure the blade in the first position and a second position different from the first position, wherein the first position allows the blade to be coupled to the handle, and wherein the blade is received from the handle in the second position and cannot be rearmed to the handle in the second position.

What is claimed is:

1. A device for coupling a blade and a handle and for decoupling a blade and a handle, the device comprising:

a housing, wherein the housing defines:
an interior chamber,
an exterior slot adjacent the interior chamber, wherein the exterior slot is dimensioned to pass the blade through the exterior slot, wherein the exterior slot is configured to receive a portion of the handle from an exterior of the housing into the interior chamber, and
a groove in the interior chamber, wherein the groove is configured to retain the blade in a ready configuration for coupling the blade to the handle; and a pivot member secured within the interior chamber of the housing, wherein the pivot member is pivotable between an unlocked configuration and a locked configuration, wherein the unlocked configuration of the pivot member is configured to allow the blade in the ready configuration to be coupled to the handle, wherein the locked configuration of the pivot member is configured to lock the blade within the interior chamber, and wherein the pivot member is disposed entirely within the interior chamber.

2. The device of claim 1, wherein the blade defines a blade slot, wherein the portion of the handle defines a raised boss configured to be received by the blade slot, and wherein the exterior slot of the housing is configured to receive the raised boss of the portion of the handle.

3. The device of claim 2, wherein the groove is oriented relative to the exterior slot to cause the raised boss of the portion of the handle to engage with the blade slot in response to receiving the portion of the handle through the exterior slot.

4. The device of claim 1, wherein the device is configured to, in response to receiving the portion of the handle through the exterior slot into the interior chamber of the housing, couple the blade in the ready configuration from the groove to the handle.

5. The device of claim 1, wherein the device is configured to, in response to receiving the blade coupled to the handle through the exterior slot into the interior chamber of the housing, decouple the blade from the handle.

6. The device of claim 5, wherein the housing defines a shelf spaced from the groove, wherein the shelf is configured to receive the decoupled blade.

7. The device of claim 6, wherein the shelf defines a shelf axis, wherein the groove defines a groove axis, and wherein the shelf axis is inclined relative to the groove axis.

8. The device of claim 1, wherein the pivot member is configured to, in response to receiving the blade coupled to the handle through the exterior slot into the interior chamber of the housing, pivot to the locked configuration.

9. The device of claim 1, wherein the pivot member comprises a flexure configured to flex about a fixed end point.

10. The device of claim 1, wherein the device further comprises a pivot pin in the interior chamber, and wherein the pivot member is configured to pivot about the pivot pin.

11. The device of claim 10, wherein the housing defines the pivot pin.

12. The device of claim 1, wherein the device further comprises a lip adjacent the exterior slot, and wherein the lip is configured to co-operate with the pivot member in the locked configuration to lock the blade within the interior chamber.

13. The device of claim 12, wherein the housing defines the lip.

14. The device of claim 1, wherein at least one of the housing and the pivot member comprises a rigid material.

15. The device of claim 14, wherein the rigid material comprises at least one of a metal, an alloy, a glass, a polymer, a ceramic, or a composite.

16. The device of claim 1, wherein the housing comprises a first housing member secured to a second housing member.

17. The device of claim 1, wherein the housing comprises the blade retained in the groove in the interior chamber, and wherein the blade is sterile.

18. The device of claim 1, wherein the housing comprises a transparent or translucent wall configured to permit visual determination whether the blade is in the ready configuration.

19. The device of claim 1, further comprising the blade disposed in the interior chamber in the ready configuration.

20. A sterile package comprising the device of claim 1.

21. A kit comprising the handle and the device of claim 1.

22. A device for coupling a blade and a handle and for decoupling a blade and a handle, the device comprising:
- a housing, wherein the housing defines:
  - an interior chamber,
  - an exterior slot adjacent the interior chamber, wherein the exterior slot is dimensioned to pass the blade through the exterior slot, wherein the exterior slot is configured to receive a portion of the handle from an exterior of the housing into the interior chamber, and
  - a groove in the interior chamber, wherein the groove is configured to retain the blade in a first position for coupling the blade to the handle;
- wherein the device comprises a catching member configured to secure the blade in the first position and in a second position different from the first position,
- wherein the first position allows the blade to be coupled to the handle,
- wherein the blade is received from the handle in the second position and cannot be rearmed to the handle in the second position, and
- wherein the catching member is disposed entirely within the interior chamber.

\* \* \* \* \*